United States Patent [19]

Vogel et al.

[11] Patent Number: 5,211,914

[45] Date of Patent: May 18, 1993

[54] TEST CARRIER FOR THE DETERMINATION OF IONS

[75] Inventors: Peter Vogel, Hemsbach; Detlef Thym, Mannheim; Michael Fritz, Rohrheimer; Dan Mosoiu, Limburgerhof, all of Fed. Rep. of Germany

[73] Assignee: Boehringer Mannheim GmbH, Mannheim, Fed. Rep. of Germany

[21] Appl. No.: 698,466

[22] Filed: May 10, 1991

[30] Foreign Application Priority Data

May 15, 1990 [DE] Fed. Rep. of Germany ....... 4015590

[51] Int. Cl.$^5$ ............................................ G01N 31/22
[52] U.S. Cl. ........................................ 422/56; 422/55;
422/57; 435/805; 436/72; 436/169; 436/170
[58] Field of Search ............... 422/56, 55, 57, 58; 436/169, 72, 170; 435/805; 428/327; 552/302, 295

[56] References Cited

U.S. PATENT DOCUMENTS

| | | | |
|---|---|---|---|
| 4,312,834 | 1/1982 | Vogel et al. | 422/56 |
| 4,552,697 | 11/1985 | Yip et al. | 552/302 |
| 4,645,744 | 2/1987 | Charlton et al. | 422/56 |
| 4,649,123 | 3/1987 | Charlton et al. | 422/56 |
| 4,670,218 | 6/1987 | Gantzer et al. | 436/74 |
| 4,780,411 | 10/1988 | Piejko et al. | 422/57 |
| 4,781,890 | 11/1988 | Arai et al. | 422/56 |

FOREIGN PATENT DOCUMENTS

| | | |
|---|---|---|
| 0016387 | 10/1980 | Europran Pat. Off. . |
| 0125554 | 11/1984 | European Pat. Off. . |
| 0153641 | 9/1985 | European Pat. Off. . |
| 0175990 | 4/1986 | European Pat. Off. . |
| 0207392 | 1/1987 | European Pat. Off. . |

OTHER PUBLICATIONS

Kirk–Othmer Encyclopedia of Chemical Technology (1982) Third Edition, vol. 17, pp. 800–801, vol. 10, pp. 210–213.

Primary Examiner—James C. Housel
Assistant Examiner—Long V. Ke
Attorney, Agent, or Firm—Felfe & Lynch

[57] ABSTRACT

The invention concerns a test carrier for the determination of ions containing a test layer which has a liquid-resistant, organic phase which contains a hydrophobic polymer in a homogeneous mixture with a hydrophobic, organic liquid of low volatility and an ionophore, as well as a substance which changes its colour in the presence of the ion to be determined. The test carrier is characterized in that the test layer contains particles with an oil number of 80-200 and the ionophore is homogeneously dispersed in the hydrophobic, organic phase.

17 Claims, 1 Drawing Sheet

TEST CARRIER FOR THE DETERMINATION OF IONS

SUMMARY OF THE INVENTION

The present invention concerns a test carrier for the determination of ions especially in aqueous liquids and especially preferably in body fluids such as blood, plasma, serum or urine.

DESCRIPTION

The determination of ions, in particular alkaline and alkaline-earth ions, in liquids is of a major importance. Attention is drawn here only to the determination of water hardness, the analysis of effluents and suchlike.

The determination of alkaline and alkaline-earth ions, in particular in body fluids, plays an important role in medical diagnostics. Thus potassium and sodium determinations are needed for the diagnosis and monitoring of cardiovascular diseases, muscle diseases, kidney diseases, shock states of different causes and suchlike. The determination of calcium is important for the diagnosis of bone diseases. Lithium determinations are necessary for the therapeutic monitoring of antidepressants containing lithium.

Ion determinations are mainly carried out with the aid of flame photometry and by means of ion selective electrodes especially in the clinical laboratory.

Apart from these a multitude of methods are known which enable the photometric analysis of ions i.e. in which the analysis reaction leads to a change in colour. A review of such methods is given in the article by M. Kolthoff "Application of macrocyclic compounds in chemical analysis" in Analytical Chemistry, 1979, 1R-22R, in particular page 16R-18R and in the literature references cited there.

These methods are based on the so-called extraction analysis. In this procedure a complexing agent (ionophore) which is selective for the type of ion to be determined is dissolved in an organic (hydrophobic) liquid which is immiscible with water. This test system is brought into intensive contact (usually it is shaken vigorously) with the aqueous sample liquid (e.g. blood, serum). In this process the ions are complexed and as a result pass into the organic phase.

Many methods for a colour test for this process are known such as in particular the use of a coloured counterionic substance which passes into the organic phase together with the analyte ions, the use of a dye which is covalently coupled to the ionophore (as a whole also denoted chromoionophore), or the use of a pH indicator located in the organic phase which releases a proton into the aqueous sample liquid in order to balance the charge when the analyte ion enters the liquid which is immiscible with water and as a result its colour changes. The latter method is denoted heterogeneous pH reaction.

Recently analysis with the aid of so-called test carriers which are also denoted rapid diagnostics and "analysis test carriers" or "solid state analysis devices" in the English language literature have become of increasing importance. They are analytical formulations in which all the reagents necessary for an analysis are present on or in absorptive carriers or films or on or in carriers or films capable of swelling and are mounted in the form of devices, so-called test carriers such as test strips or slides, which are simple to use. After they have been wetted with the sample, such as a body fluid, the test reaction proceeds. A colour formed which is a measure for the amount of analyte to be determined can then be evaluated with the aid of a colour comparator panel or with simple reflectance photometers.

A particular feature of rapid diagnostics is their simple handling. As a consequence, results of the highest accuracy are achieved even when used by less well trained laboratory personnel or even by the patients.

In view of these advantages there has not been a lack of attempts to also develop rapid diagnostics for the analysis of ions whereby in this case approaches which are known from classical test tube analysis have also been used.

Test carriers which are based on the principles of ion selective electrodes are for example known from the U.S. Pat. No. 4,171,246. However, their construction is relatively complicated and their handling is made especially difficult by the necessity to correctly apply a reference liquid, in addition to the sample liquid, onto the appropriate position of the test carrier.

The application of extraction analysis to test carriers is described in U.S. Pat. No. 3,635,679 and is exemplified by divalent metal ions. In this process a film layer (analysis film) based on a hydrophobic polymer (in particular polyvinyl chloride) is used which contains a hydrophobic organic liquid as an additional film-forming component which is usually used as a plasticizer for plastic foils. EP-B-0 041 175 is concerned with the application of the same reaction principles for alkaline metals.

The use of an analysis film with the said film-forming components in principle enables the analysis of ions with the aid of a rapid diagnostic. However, in practice great difficulties arise which are probably mainly the result of the slow exchange between the aqueous sample liquid and the hydrophobic analysis film. In particular the formation of colour is not intensive enough so that only a relatively small signal amplitude is obtained and as a consequence a relatively poor precision of the analysis. In addition a defined colour change with a constant final value is not observed to the extent which would be desirable for an analysis using an end-point determination.

Therefore already very many special test layer structures have been proposed which are intended to make improvements in this respect.

An operational design is described in EP-A-0 125 555 in which the organic phase is present as a plasticized, non-polar, non-porous plastic film in which the ionophore and indicator are dissolved. It is apparent from the examples that the test reaction does not come to a standstill and thus the determination of the ions is only possible by kinetic measurements. This is a particular disadvantage when it is intended to measure without the employment of a standard which is usual with rapid diagnostics. Kinetic measurements are then very susceptible to ageing of the diagnostic agents. In addition the examples merely disclose tests for aqueous solutions with upper concentrations limits of up to 3 mmol potassium/1 which is diagnostically inadequate for the analysis of serum and which necessitates a dilution of the sample. Serum of healthy individuals has potassium concentrations of about 3.5 to 5.5 mmol/1.

An application design is described in EP-A-0 125 554 in which the organic hydrophobic phase is embedded in a hydrophilic matrix in the form of small droplets. The disclosed reaction times of more than two minutes are, however, relatively long for a rapid diagnostic. In addition experience shows that such emulsions are difficult to produce reproducibly and also to keep in a dry state especially over long time periods. Also in this case, according to the examples the analysis of potassium requires a pre-dilution.

EP-A-0 141 647 describes a test device, in particular for the determination of an ionic analyte in a liquid, containing reflecting particles with no interstitial volume which are held together by a polymeric binding agent. An extraction agent for the analyte and a detection agent, for example a chromoionophore, are located on the surface of the particles. The polymeric binding agent per se must be permeable to the analyte or reaction products of the analyte. As shown in the examples, test devices of this type require reaction times of about five minutes. Such times are too long for a rapid diagnostic.

EP-A-0 153 641 describes a porous carrier matrix which is impregnated with an organic, hydrophobic phase containing chromophore and ionophore. Paper is described as the preferred carrier matrix. However, experience shows that papers have a relatively inhomogeneous composition and consequently the necessary precision, in particular for the potassium determination, cannot always be obtained. Thus it is mentioned in the said application that coefficients of variation up to 4% are obtained.

In U.S. Pat. No. 4,780,411 hydrophilic, preferably water-soluble particles of appropriate organic polymers are embedded in an organic phase made of hydrophobic, film-forming, water-insoluble polymer.

The object of the present invention is to provide a rapid test for the determination of ions which is characterized by a rapid reaction and intensive colour formation and by a correspondingly increased precision of the analysis.

This object is achieved by the invention characterized in the patent claims and described herein.

The invention provides a test carrier for the determination of ions. It contains a test layer which has a liquid-resistant organic phase which in turn contains a hydrophobic polymer in a homogeneous mixture with a liquid of low volatility which is immiscible with water. Furthermore the test carrier contains an ionophore and a chromogen which changes its colour in the presence of the ion to be determined. The test carrier according to the present invention is characterized in that the test layer contains particles with an oil absorption value of 80–200, preferably 100–170 and the ionophore is homogeneously dispersed in the hydrophobic organic phase.

The test layer of the test carrier according to the present invention has a highly porous structure. Since in contrast to EP-A-0 153 641, a carrier matrix is not necessary, the problems caused by the structure of the matrix material are avoided in the optical evaluation. In addition the test layer according to the present invention can be manufactured relatively easily which results in economic advantages.

By using the test layer according to the present invention, only a very short reaction time is necessary. The colour formation is already complete after about 60 seconds, so that from a practicle standpoint an endpoint determination can be carried rut easily.

Test layers which contain organic or inorganic particles embedded in a polymeric material are known. Thus for example the use of different particles to produce a porous spreading layer is described in the U.S. Patent Specification 3,992,158. EP-B-0 016 387 is directed to an analysis layer in which the inorganic or organic particles are used in a particular size and concentration range as film opener. EP-B-0 013 156 describes a particle composite structure in which the organic polymeric particles are linked with the aid of a small amount of binding agent to form an open-pore composite structure. However these publications give no reference to the solution of the specific problems in the analysis of ions which have been the subject of endeavours in professional circles for many years.

The test layer according to the present invention, which can also be denoted film layer, contains a liquid-resistant film made of a hydrophobic polymer and particles dispersed therein. The hydrophobic polymer is impervious to the liquid to be examined and also to the ions to be determined. It is the particles which enable the sample liquid to penetrate into the test layer. The test layer as a whole is impervious to the liquid to be examined. A certain volume is merely taken up. In particular copolymers of vinyl acetate have proven to be advantageous for use as the hydrophobic polymers. Copolymers of vinyl acetate with vinyl laurate or maleic acid dibutyl ester are particularly advantageous.

Solid, insoluble, inert, inorganic or organic particles which are insoluble in the liquids to be examined and which have an oil absorption value of 80–200, preferably 100–170 can be used as the particles. Above all the different types of diatomaceous earths such as unbaked or natural kieselguhr, calcinated or baked kieselguhr, flow-baked or activated kieselguhr have proven to be advantageous for the film layer according to the present invention.

The oil absorption value is a well known parameter in the field of paints and coatings for particles which are for example used as fillers. It is a measure of the interaction between the particles and the medium in which they are dispersed. The oil absorption value is simple to determine. The determination is carried out according to DIN (German Industrial Standard) 53199. According to this norm the oil absorption value indicates the amount of linseed oil in g which is needed in order to process 100 g of the particles of interest into a coherent putty-like mass. For this the particles (weight "a" in g) are placed on a glass plate. About ⅔ of the required amount of linseed oil is added from a burette. Oil and particles are processed under pressure by intensive rubbing with a spatula until the mixture is homogeneous. Then oil is again added dropwise and is processed each time in the same manner until a coherent, putty-like mixture is formed which just does not smear on the glass plate. The amount "b" in ml of oil consumed in this is measured to 0.01 ml. The oil absorption value is then calculated from the following formula:

$$\text{oil absorption value} = \frac{0.93 \times b \times 100}{a}$$

In this 0.93 denotes the density of the linseed oil in g/ml.

As a rule the particle is used have a non-uniform shape. Their particle size is usually between 0.1 and 200 μm, preferably between 0.2 and 30 μm. A particular feature of the particles used according to the present invention is that they have cavities into which gases and wetting liquids can penetrate. An expression of this property is in particular the low bulk density of 50 to 250, preferably 80 to 180 g/l.

A ratio by weight of hydrophobic polymer to particles of about 5:1 to 1:10 is useful for the film layer according to the present invention. The ratio by weight is preferably about 1:1 to about 1:3. The optimal ratio by weight of hydrophobic polymer to particle is in each case dependent on the nature of the polymer used and the particles. If the hydrophobic polymer is a copolymer of vinyl acetate with vinyl laurate and/or maleic acid dibutyl ester and the particles are diatomaceous earths, the optimal ratio by weight is between 1:1.5 and 1:2.5.

Further necessary constituents of the film layer according to the present invention are a liquid of low volatility which is immiscible with water and an ionophore. These components are dispersed homogeneously in the hydrophobic polymer.

A liquid of low volatility which is immiscible with water is understood as a plasticizer for plastics. It serves, together with the polymer, as the organic phase for the method of determination of ions. All possible commercial types of plasticizer, preferably esters of sebacic acid, acrylic acid, phthalic acid and phosphoric acid, as well as silicons come into consideration. In particular for technical reasons concerning the processing, the liquid of low volatility known as Uvinul ® N539 (2,2-diphenyl-1-cyano-acrylic acid ethylhexyl ester) is preferred.

The ratio by weight of hydrophobic polymer to the, hydrophobic, organic liquid of low volatility in the test layer can be between about 5:1 to about 1:5, in particular between about 2:1 to about 1:2.

All those substances which can complex ions can be used as the ionophore which are specific for the ions to be determined and sufficiently soluble in a non-aqueous phase. In this connection crown ethers, cryptands, podands and corresponding peptides of a cyclic or acyclic nature come into consideration. 2,3-naphthol-15-crown-5 has proven to be particularly advantageous for the determination of potassium. The natural ionophore valinomycin is especially preferred. For the determination of sodium, N,N'-dibenzyl-N,N'-diphenyl-1,2-phenylene-dioxydiacetamide comes for example into consideration, for lithium, N,N'-diheptyl-5,5-dimethyl-N,N'-di(3-oxapentyl)-3,7-dioxanonane-diamide and for calcium, diethyl-N,N'-[(4R,5R)-4,5-dimethyl-1,8-dioxo-3,6-dioxa-octamethylene]-bis-(12-methylaminododecanoate).

The test carrier according to the present invention contains as an essential component a substance which changes its colour in the presence of the ion to be determined. Potential appropriate substances were already mentioned in the introduction. Such substances can in principle be present in the test layer according to the present invention or in a second test layer. In the case of the second alternative it must, however, be possible to bring the two layers into a direct or indirect contact with one another so that an exchange of liquid is possible. Although a counterion dye is preferably not in the test layer according to the present invention but is rather incorporated into another layer, a chromoionophore can also be present in the test layer according to the present invention. A pH indicator will be present in the test layer according to the present invention. It is preferably homogeneously dispersed in the hydrophobic organic phase there just as the ionophore. The use of pH indicators according to the principle of the heterogeneous pH reaction is particularly preferred according to the present invention. This principle can be shown diagramatically as follows:

As already described above ionophores are complexing agents for ions and have to be soluble in organic substances which are immiscible with water for the above principle. The usual organo-soluble pH indicators come into consideration as the H indicators. The ionophore and pH indicator can also be present covalently linked as a so-called chromoionophore. The principle functions as follows: An ion from the aqueous phase to be examined is pulled into the organic phase which is immiscible with water using the ionophore. In order to balance the charge, a proton must be released into the aqueous phase. This proton is taken from the pH indicator which as a result forms a coloured anion.

This principle was first mentioned by E. S. Hyman, Biophysical Society Abstracts, 1971, 72a and namely uses valinomycin as the ionophore and tetrabromophenolphthalein ethyl ester as the pH indicator. Descriptions with chromoionophores may for example be found in K. Ueno and M. Tagaki, Studies in Physical and Theoretical Chemistry 27, 279–293 (1982) as well as in H. Nakamura et al., Bunseki Kagaku 31, E 131–E 134 (1982).

According to the present invention those pH indicators can be used which are soluble in non-aqueous media and are so hydrophobic that they are not extracted out of the organic phase into an aqueous phase under the analytical conditions. According to the principle shown for the determination of ions, the pK value should be such that the indicator substance can release protons under the analytical conditions in the presence of the ion to be determined and as a result undergoes a change in its coloured state. Tetrabromophenolphthalein esters can for example be used as described in E. S. Hyman, Biophysical Society Abstracts, 1971, 72a or alkylindonaphthols as disclosed in U.S. Pat. Nos. 4,552,697 and 4,540,520.

Chromoionophores which are present as a covalently-bound combination of an ionophore and a pH indicator can also be used. For the determination of potassium, 4'-(2",4"-dinitro-6"-trifluorophenylmethyl)-amino-benzo-18-crown-6 has for example proven to be advantageous. The corresponding 15-crown-5 compound can be used for the determination of sodium.

A naphthol derivative having the general formula I is preferred as the pH indicator:

(I)

in which

R$^1$, R$^2$, R$^3$ are the same or different and each represents hydrogen, an alkyl or alkoxy group in which at least one of the residues is a (C$_8$–C$_{30}$)-alkyl or alkoxy residue, R$^4$ is hydrogen or an alkyl group, R$^5$ is a nitro group, an alkyl group substituted by halogen, a cyano group, a sulfonamide group or an alkylsulfonyl group, X is nitrogen or the residue CR$^6$ and Y is sulphur or the residue CR$^7$=CR$^8$ in which R$^6$, R$^7$, R$^8$ are the same or different and denote hydrogen, halogen, a nitro group, a cyano group, an alkyl group or an alkyl group substituted by halogen or an alkylsulfonyl group. Such substances are described in DE-A-4015591.9.

An alkyl group in the definition of the residues R$^1$, R$^2$, R$^3$, R$^4$, R$^6$, R$^7$ and R$^8$ is understood as an alkyl residue with 1 to 30 carbon atoms. It is preferred that in particular the residues R$^4$, R$^6$, R$^7$ and R$^8$ be alkyl residues with 1 to 4 carbon atoms and in a particularly preferred embodiment have 1 to 2 carbon atoms. Concerning the residues R$^1$, R$^2$ and R$^3$, only one of the residues is preferably an alkyl residue with 8 to 30, preferably with 10 to 20 carbon atoms. If the other residues in this group also represent an alkyl group, then they are preferably alkyl residues with 1 to 4, most preferably 1 to 2 carbon atoms. Alkyl residues with more than 2 carbon atoms can be straight-chained or branched. In addition the alkyl residue can also be partially unsaturated.

An alkyl group substituted by halogen in the definition of R$^5$, R$^6$, R$^7$ and R$^8$ is understood as an alkyl residue with 1 to 4 carbon atoms substituted by fluorine, chlorine, bromine or iodine. Alkyl residues with 1 to 2 carbon atoms substituted by fluorine are preferred. The trifluoromethyl residue is particularly preferred.

An "alkoxy group" as used for residues R$^1$, R$^2$, R$^3$ is an alkoxy residue with 8 to 30, preferably 10 to 20 carbon atoms. The alkoxy residue can be straight-chained or branched, saturated or partially unsaturated.

Halogen in the definition of the residues R$^6$, R$^7$, R$^8$ can denote fluorine, chlorine, bromine or iodine; chlorine and bromine are preferred.

An alkylsulfonyl group in the definition of the residues R$^5$, R$^6$, R$^7$, R$^8$ denotes the group alkyl—SO$_2$—. In this connection the alkyl group represents an alkyl residue of 1 to 4, preferably 1 to 2 carbon atoms. The methylsulfonyl group is particularly preferred.

A sulfonamide group in the definition of the residue R$^5$ is understood as an unsubstituted amine (—SO$_2$NH$_2$) or an amide of a primary or secondary amine (—SO$_2$NHR or —SO$_2$NR$_2$). Alkyl, aryl or aralkyl residues can be substituents (R) of the amide. In the case of the amide of a secondary amine, the substituents (R) can be the same or different. An alkyl residue in this connection is understood as a residue with 1 to 4 carbon atoms. An aryl residue denotes an aromatic residue with 6 to 10 carbon atoms. Preferred aryl residues are phenyl or naphthyl residues. Aralkyl residues are those residues in which the aryl moeity is an aromatic residue with 6 to 10 carbon atoms and the alkyl moeity is a residue with 1 to 4 carbon atoms. The benzyl residue is a preferred aralkyl residue. The unsubstituted sulfonamide group (—SO$_2$NH$_2$) is particularly preferred for the present invention.

Particularly preferred naphthol derivatives having the general formula I are those in which one of the residues R$^1$, R$^2$ and R$^3$ represents an alkyl or alkoxy residue with 8 to 30, preferably 10 to 20 carbon atoms and the other residues of the aforementioned group denote hydrogen or an alkyl residue with 1 to 4, preferably 1 to 2 carbon atoms.

Particularly preferred naphthol derivatives are those in which R$^1$ represents an alkoxy group with 10 to 20 carbon atoms and R$^2$ and R$^3$ represent hydrogen and the other residues have the meaning stated for formula I.

Several variants of the process for the production of naphthol derivatives having the general formula I are possible. Firstly naphthoquinones having the general formula II (II)

in which R$^1$, R$^2$ and R$^3$ have the meaning stated for the general formula I are reacted with a hydrazine having the general formula III (III)

in which R$^4$, R$^5$, X and Y have the meaning stated for the general formula I. This reaction can take place under the usual conditions for the formation of a hydrazone. The reaction preferably takes place under acidic conditions. The hydrazone per se in unstable and rearranges to form the desired naphthol having the general formula I.

Another method for the production of the naphthol derivative having the general formula I starts with amines having the general formula IV (IV)

in which R$^4$, R$^5$, X and Y have the meanings stated for the formula I. These amines are diazotized and the resulting diazonium salts are reacted in an azo coupling reaction with a naphthol having the general formula (V)

(V)

in which $R^1$, $R^2$ and $R^3$ have the meaning stated for the general formula I.

The diazotization of the amines having the general formula IV can take place in the usual manner. It has proven to be advantageous to prepare concentrated mineral acids, for example concentrated sulphuric acid with a nitrite, preferably sodium nitrite and then to add the amine having the general formula IV while cooling to room temperature. A diazotization mixture which also contains glacial acetic acid apart from sodium nitrite and concentrated sulphuric acid has proven to be especially advantageous. The preferred volume ratio of sulphuric acid and glacial acetic acid is between 1:1 and 2:1. The ratio of nitrite and the amine to be diazotized having the general formula IV is usually equimolar.

After completion of the diazotization reaction the reaction mixture is processed in an aqueous solvent. For this purpose the reaction mixture is preferably poured onto iced water. The diazonium salt per se is not isolated but is made to azo-couple with the naphthol having the general formula V in the aqueous processing solution. This is preferably carried out under weak acidic conditions. Naphthols having the general formula V are only very sparingly soluble in aqueous solutions. They are therefore applied in organic solvents.

Chloroform is for example well suited as the organic solvent. In this way a diazonium said solution which is present after the aqueous processing can be added to a solution of a naphthol having the general formula V in chloroform and glacial acetic acid, and an acetate can be added to buffer the pH value of the reaction medium. In most cases the naphthol derivatives which form having the general formula I precipitate out of the reaction mixture. The product can then be re-crystallized or purified chromatographically.

In particular when using pH indicators, it is particularly advantageous to incorporate a buffer in the film layer of the present invention because of the indicators' natural sensitivity to pH changes. In determination methods for ions which are based on the heterogeneous pH reaction described on page 9, the pH of a buffer controls the transfer of the proton from the non-aqueous into the aqueous phase. It therefore depends on the pK value of the pH indicator used. In diagnostic agents for the determination of ions in body fluids the buffer substance is preferably chosen so that the pH can be adjusted to a value between 5-10, preferably between 7 to 8. In principle all the usual buffers come into consideration for this, provided they are soluble in water and do not contain ions which interfere with the test reaction. Buffers have proven to be suitable which are from the so-called Good buffer series such as e.g. N,N-bis-(hydroxyethyl)-aminoethanesulfonic acid (BES), 3-[N-trishydroxymethyl]-methylamino-hydroxypropane-sulfonic acid (TAPSO) or N-hydroxyethylpiperazine-N-propanesulfonic acid (HEPPS).

If ionophores are used which are not sufficiently selective for the ion to be determined then water soluble complexing agents can be added which mask the interfering ions. Thus, for example a possible interference of a sodium test by calcium is prevented with ethylenediaminetetraacetate (EDTA).

In addition wetting agents can be used to improve the production of the films or the wetting of the films by the sample to be examined. Only those agents can be used for this which do not interfere with the test reaction. These are in particular non-ionic and zwitterionic compounds. Of the non-ionic wetting agents, polyethylene glycol ethers or esters, preferably Triton ® X100, have for example proven to be advantageous. n-Decyl-N,N-dimethyl-3-ammonio-1-propanesulfonate (Zwittergent ® 3-10) can be used advantageously as a zwitterionic wetting agent.

In order to improve the consistency of the film layer according to the present invention, &thickeners can additionally be used. Ethylcellulose has proven to be particularly advantageous for this. In addition to this hydrophilic thickening agents, such as for example hydroxyethyl- or hydroxypropylcellulose, can also be added to the test layer according to the present invention for the aqueous phase which is present after wetting the film layer according to the present invention with an aqueous liquid to be analyzed.

In order to produce a film layer according to the present invention, all components which, when the film layer is used for the determination of an ion in an aqueous liquid, in particular in a body fluid such as blood, plasma, serum or urine, should not be taken up in the aqueous phase but rather should remain in the organic phase i.e. the film layer (hydrophobic polymer; difficultly volatile liquid which is immiscible with water; ionophore; if desired a chromogen, such as a pH indicator, and if desired, a thickener for improving the consistency of the film layer) are dissolved in a highly volatile to moderately volatile organic solvent. The particles are stirred into this solution and dispersed homogeneously therein. Afterwards the paste is spread out on a support with a doctor blade and dried. Of course other suitable methods of application can also be used such as roll coating, film casting or similar procedures. The dry film layer has a thickness of 20 to 500, preferably of 20 to 150 $\mu$m.

There are different ways of incorporating components (buffer; if desired complexing agent; if desired wetting agent; if desired thickener for charging the consistency of the aqueous phase) which are taken up into the aqueous phase when the aqueous sample liquid is applied to the film layer according to the present invention. One possibility is to coat the particles with the aforementioned components by evaporating, spray drying or freeze drying the particles together with an aqueous solution of the components. The particles coated in this way are then stirred into the organic solvent as described above. Another possibility), is to first produce the film layer with untreated particles, then to re-coat with an aqueous solution of the aforementioned components and finally to dry.

The film layer is preferably used together with the base as carrier. In particular the film layer according to the present invention can be processed further to known application forms such as those which have been described many times for rapid diagnostics. They are for example simple test carriers, in which the test film is glued to the end of a narrow, stiff strip, for example of plastic.

It can also be advantageous for a test carrier, which also contains one or several other layers apart from the test layer according to the present invention, not to place those components in the film layer according to the present invention which can be taken up in the aqueous phase during the determination reaction but rather to completely separate them from it. A consequence can for example be that these components are applied to another carrier layer, for example a paper layer or a net.

The evaluation of a test using a test carrier according to the present invention can be carried out visually as well as by reflectance photometry in a known manner.

It has proven to be particularly advantageous for the accuracy, in particular of the evaluation by reflectance photometry, when the film layer contains an organic acid which is readily soluble in a non-aqueous medium. Such a process is described in DE-A-4015592.7. Higher nitrated alkylphenols or higher nitrated alkoxynaphthols or carbonyldicyanidophenylhydrazones have proven to be very especially advantageous. Such substances are able to match the range of highest measurement sensitivity to the relevant concentration range of the ion to be determined. Bis-(2-hydroxy-3,5,6-trichlorophenyl)-methane (hexachlorophene), 3-pentadecyl-2,4,6-trinitrophenol and 2,4,6,8-tetranitro-5-octadecyloxynaphthol-1 as well as [(2,4-dinitrophenyl)-hydrazono]propanedinitrile (mesoxalic acid-dinitrile-2,4-dinitrophenyl-hydrazone) have proven to be particularly valuable in this connection.

The following Table 1 indicates the advantageous and preferred percentages by weight of the components of a test layer according to the present invention:

TABLE 1

| Component of the film layer | Content of the film layer in % by weight | |
| --- | --- | --- |
| | advantageous | preferred |
| polymer | 5–60 | 20–40 |
| the liquid of low volatility is immiscible with water | 5–70 | 20–40 |
| particles | 15–80 | 30–50 |
| ionophore | 0.05–5.0 | 0.2–1.0 |

If the buffer substance is applied in or onto the film layer according to the present invention then this contains 5–30, preferably 10–20% by weight buffer. If the test layer according to the present invention contains a chromogen, such as for example a pH indicator, then it is present there in an amount of about 0.05–5.0, preferably 0.2–0.7% by weight. The substances which can be used, if desired, such as complexing agents, wetting agents or thickeners or acid for increasing the sensitivity, are in amounts—if they have been applied in or onto the film layer according to the present invention—of 0.005 to 5, preferably 0.02 to 2% by weight of the film layer according to the present invention.

Figure 1:
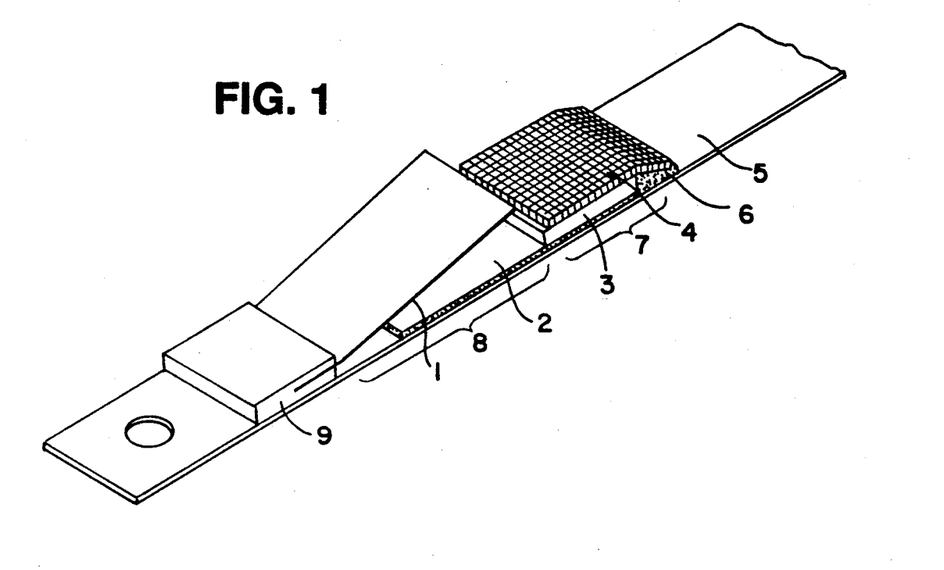
FIGS. 1 and 2 show test carriers for the determination of Potassium.
Figure 2:
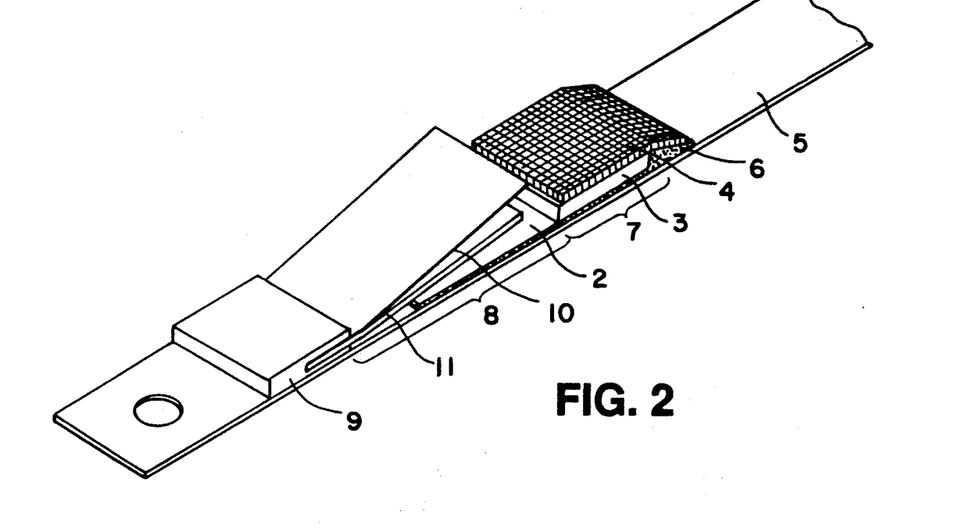

Particularly advantageous design forms of a test carrier according to the present invention for the determination of ions in liquids are shown in the FIG. 1 and 2 which contain a film layer according to the present invention.

FIG. 1 shows a particularly preferred test carrier with a film layer according to the present invention.

FIG. 2 shows a further especially preferred test carrier with a film layer according to the present invention.

Two test carriers are shown spatially in FIGS. 1 and 2 which are suitable for the determination of ions in blood. They allow the serum or plasma to be isolated from whole blood and the determination of the ions of interest in the liquid obtained in this way. The test carriers differ mainly in the location of the buffer substance within the test carrier. Details of the composition of the devices are as follows:

FIG. 1: A transport layer (2) which serves to transport the sample liquid from the sample application zone (7) into the test zone (8) is fixed onto an inert carrier foil (5), for example a plastic foil. In principle any material is suitable as the transport layer (2) which is able to transport the liquid to be examined from the sample application zone (7) into the test zone (8) and which in this process do not alter it in such a way that the analysis becomes impaired. It is particularly preferable to use a glass fibre fleece as the transport layer (2). A layer (3) for the separation of corpuscular components from the sample liquid is attached to the transport layer (2) and partially covers it. Basically any material can be used for this which enables corpuscular components from the sample liquid, in particular blood cells, and above all erythrocytes from blood, to be separated off and does not allow them to reach the test zone (8) in substantial amounts in order that they do not cause an interference in the test reaction there. In addition the separating layer (3) should not lead to a change in the sample liquid such that the concentration therein of the ions to be determined is changed and thus the result is falsified. Glass fibre fleeces, such as those described e.g. in EP-B-0 045 476, have proven to be particularly suitable for the separating layer (3). A protective layer (4) is mounted over the separating layer (3) which is intended to prevent damage of the separating layer (3) during the sample application, for example with a pipette. A net of inert material, for example of plastic, has proven to be of value for this. The protective layer (4) and separating layer (3) are fixed onto the inert carrier foil (5). This can for example be carried out by means of a strip of hot-melting adhesive (6). A carrier foil consisting of transparent plastic with the test layer according to the present invention (1) is attached to one side of the transport layer (2) This is preferably effected by a glued joint (9) for example a strip of hot-melting adhesive. The film layer (1) is positioned so that it can be brought into contact with the transport layer (2) in such a way that liquid transfer is possible by pressing the transparent carrier foil towards the inert carrier foil (5).

FIG. 2 differs from FIG. 1 in that a layer (11), which contains those substances which are taken up into the aqueous phase during the determination reaction, is mounted between the film layer (10) and transport layer (2) likewise via the glued joint (9) which is for example a strip of hot-melting adhesive. Such substances include buffer substances. Complexing agents, wetting agents or thickeners for altering the consistency of the aqueous phase can also be incorporated into the additional layer (11) of FIG. 2 instead of in the film layer (I) of FIG. 1 or (10) of FIG. 2. Absorptive materials may be used as materials for the additional layer (11) which enable a liquid transfer to a further layer when this is brought into contact with it. Paper is particularly preferred, but nets or fabrics made of inert materials such as plastic may also be used.

In order to carry out the determination of an ion in blood by means of one of the test carriers shown in the figures, the sample is applied to the protective layer (4). The blood penetrates into the separation layer (3) and erythrocytes are separated from plasma or serum. The liquid obtained in this way is sucked into the test zone (8) by capillary forces. The aqueous phase in the transport layer (2) is brought into contact with the film layer by pressure on the carrier foil with the film layer (1) or (10), according to the present invention. Liquid penetrates into the film layer and the determination reaction is triggered. The colour formed in the film layer resulting from the reaction is observed visually or measured by reflectance photometry through the carrier foil of the film layer (I) or (10).

The invention is elucidated further in the following examples.

EXAMPLE 1

General instructions for the production of test carriers with a film layer according to the present invention For the production of a test carrier according to FIG. 1, transparent polyester foil (200 μm thick) is coated with the mixtures mentioned in the following examples and dried. The coated foil is cut into 15 mm wide strips and glued longitudinally as layer (1) with hot-melting adhesive onto 150 mm wide white polyester foil (5). Strips of glass fibre fleece with an area weight of 30 g/m² as transport layer (2), of glass fibre fleece with an area weight of 60 g/m² as separation layer (3) and of polyamide fabric as protective layer (4) are also glued longitudinally onto this white polyester foil so that after cross-cutting 6 mm wide test strips according to FIG. 1 are formed.

Test carriers according to FIG. 2 are produced analogously. The layer (11) consists of filter paper which is impregnated with a buffer substance.

The film layer or test carrier according to the present invention may be used in such a way that 30 μl of the sample to be examined is applied to the polyamide fabric (4) and the test carrier is then inserted into the commercial reflectance photometer Reflotron$^R$ (Boehringer Mannheim GmbH, Mannheim, Federal Republic of Germany). The liquid penetrates into the glass fibre fleece (3), where in the case of whole blood the erythrocytes are separated, and reaches the glass fibre zone (2) which serves as the transport layer. In the reflectance photometer the film under the flap (1) or (10) is brought into contact with the liquid in the transport layer (2) by pressure on the flap and the colour formed is measured by reflectance photometry at 642 nm and 37° C.

EXAMPLE 2

Film layers according to the present invention

Mixtures of the following composition are produced and applied with a wet film thickness of 300 μm to transparent polyester foils and dried:

| | |
|---|---|
| 2,2-diphenyl-1-cyano-acrylic acid-ethylhexyl ester (Uvinul ® N539, BASF, Ludwigshafen, Germany) | 6.42 g |
| 4-(2,6-dibromo-4-nitro-phenylazo-)-2-octadecyloxy-naphthol-1 (Example 5a-c) | 0.69 g |
| Valinomycin | 0.107 g |
| Diatomaceous earth (Celatom ® MW 25, Eagle-Picher, Cincinatti, USA) | 10.05 g |
| Methyl-ethyl ketone | 18.1 g |
| Vinyl acetate-vinyl laurate copolymer (Vinnapas ® B 500/20 VL, Wacker Chemie, Munich, Germany) | 5.24 g |

A second layer of the following composition having a wet film thickness of 150 μm is applied to these layers and dried in the same way.

| | |
|---|---|
| N,N-bis-(hydroxyethyl)-aminoethanesulfonic acid | 81.13 g |
| Hydroxyethyl cellulose (Natrosol ® 250 G, Hercules Inc., Wilmington, Delaware, USA) | 4.81 g |
| Water | 236 g |
| Ethanol | 334 g |
| adjusted to pH 7.5 with LiOH. | |

Test carriers according to FIG. 1 are produced from the coated foil as described in Example 1 and measured. The measurement is carried out with serum with 5.06 mmol potassium/l at intervals of 4 seconds after the sample contacts the film layer according to the present invention.

TABLE 2

| Seconds | % Reflectance |
|---|---|
| 4 | 24.8 |
| 8 | 21.7 |
| 12 | 20.0 |
| 16 | 19.2 |
| 20 | 18.6 |
| 24 | 18.2 |
| 28 | 17.9 |
| 32 | 17.7 |
| 36 | 17.5 |
| 40 | 17.4 |
| 44 | 17.2 |
| 48 | 17.1 |
| 52 | 17.0 |
| 56 | 16.9 |
| 60 | 16.9 |
| 64 | 16.8 |
| 68 | 16.8 |

It can be seen that an adequate colour constancy with a sufficient colour intensity is reached after 60 seconds.

EXAMPLE 3

Test carrier for the determination of potassium according to FIG. 1 a) A mixture of the following composition is produced and applied with a wet film thickness of 300 μm to a transparent polyester foil and dried:

| | |
|---|---|
| Vinyl acetate-vinyl laurate copolymer (Vinnapas ® B 500/20 VL, Wacker Chemie, Munich, Germany) | 13.11 g |
| 2,2-diphenyl-1-cyano-acrylic acid-ethylhexylester (Uvinul ® N539, BASF, Ludwigshafen, Germany) | 16.04 g |
| 4-(2,6-dibromo-4-nitro-phenylazo-)-2-octadecyloxy-naphthol-1 Example 5a-c) | 0.173 g |
| 2,4,6,8-tetranitro-5-octadecyloxy-naphthol-1 (Example 6) | 0.0456 g |
| Valinomycin | 0.2673 g |
| Diatomaceous earth (Celatom ® MW 25, Eagle-Picher, Cincinatti, USA) | 25.13 g |
| Butyl acetate | 45.17 g |

A second layer of the following composition having a wet film thickness of 150 μm is applied to this layer and dried in the same way.

| | |
|---|---|
| N,N-bis-(hydroxyethyl)-aminoethane-sulfonic acid | 81.13 g |
| Hydroxyethyl cellulose (Natrosol ® 250 G, Hercules Inc., Wilmington, Delaware, USA) | 4.81 g |
| Water | 236 g |
| Ethanol | 334 g |
| adjusted to pH 7.5 with LiOH. | |

Test carriers according to FIG. 1 are produced from the coated foil as described in Examples 1 and 2, and measured. The measurement is carried out 60 seconds after the sample contacts the film layer according to the present invention.

When sera are used with different contents of potassium, the following dependence of the reflectance (%R) on the potassium content is found:

TABLE 3

| Potassium content [mmol potassium/l] | Reflectance (% R) |
| --- | --- |
| 0.24 | 60.2 |
| 1.09 | 53.5 |
| 1.87 | 48.0 |
| 3.18 | 40.3 |
| 4.15 | 36.3 |
| 6.08 | 29.9 |
| 8.10 | 25.3 |
| 10.22 | 22.2 |
| 12.10 | 19.8 |

If the measurements are carried out several times and the %R values are converted into concentrations by means of a calibration curve, then coefficients of variation between 1 and 2% are obtained.

b) A mixture of the following composition is produced and applied with a wet film thickness of 300 μm to a transparent polyester foil and dried:

| | |
| --- | --- |
| Vinyl acetate-maleic acid dibutylester copolymer (Mowolith ® 35/73, Hoechst AG, Frankfurt, Germany) | 14.7 g |
| 2,2-diphenyl-1-cyano-acrylic acid-ethylhexylester (Uvinul ® N539, BASF, Ludwigshafen, Germany) | 18.4 g |
| 4-(2,6-dibromo-4-nitro-phenylazo-)-2-octadecyloxy-naphthol-1 (Example 5a–c) | 0.130 g |
| Valinomycin | 0.600 g |
| Diatomaceous earth (Celatom ® MW 25, Eagle-Picher, Cincinatti, USA) | 28.2 g |
| Butyl acetate | 50.7 g |

A second layer of the following composition having a wet film thickness of 150 μm is applied to this layer and dried in the same way.

| | |
| --- | --- |
| Hydroxyethyl cellulose (Natrosol ® 250 G, Hercules Inc., Wilmington, Delaware, USA) | 41.5 g |
| N,N-bis-(hydroxyethyl)-aminoethanesulfonic acid | 8.5 g |
| Ethanol | 64 ml |
| adjusted to pH 7.8 with LiOH. | |

Test carriers according to FIG. 1 are produced from the coated foil as described in examples 1, 2 and 3a), and measured. The measurement is carried out 60 seconds after the sample contacts the film layer according to the present invention.

When sera are used with different contents of potassium, the following dependence of the reflectance (% R) on the potassium content is found:

TABLE 4

| Potassium content [mmol potassium/l] | Reflectance (% R) |
| --- | --- |
| 1.00 | 33.4 |
| 1.98 | 28.5 |
| 2.99 | 25.1 |
| 4.12 | 22.7 |
| 6.00 | 19.3 |
| 8.04 | 17.1 |
| 10.12 | 15.4 |
| 11.98 | 14.3 |

EXAMPLE 4

Test carrier for the determination of potassium according to FIG. 2

A mixture of the following composition is produced and applied with a wet film thickness of 300 μm to a transparent polyester foil and dried:

| | |
| --- | --- |
| Vinyl acetate-vinyl laurate copolymer (Vinnapas ® B 500/20 VL, Wacker Chemie, Munich, Germany) | 19.6 g |
| 2,2-diphenyl-1-cyano-acrylic acid-ethylhexylester (Uvinul ® N539, BASF, Ludwigshafen, Germany) | 24.0 g |
| 4-(2-bromo-4-nitro-6-trifluoromethylphenylazo-)-2-octadecyloxy-naphthol-1 (Example 5d) | 0.071 g |
| Mesoxalic acid-dinitrile-2,4-dinitrophenyl-hydrazone (Example 8) | 0.052 g |
| Valinomycin | 0.30 g |
| Diatomaceous earth (Celatom ® MW 25, Eagle-Picher, Cincinatti, USA) | 37.5 g |
| m-Xylol | 67.4 g |

Long-fibre paper 6776 (Schöller and Hösch, Gernsbach, Federal Republic of Germany) is impregnated with the following solution and dried:

| | |
| --- | --- |
| N,N-bis-(hydroxyethyl)-aminoethanesulfonic acid | 8.5 g |
| n-Octylglucoside | 0.1 g |
| Water, dist. | 91.5 ml |
| adjusted to pH 7.5 with LiOH. | |

Test carriers according to FIG. 2 are produced from the coated foil (10) and the impregnated paper (11) as described in Example 1 and measured. The measurement is carried out 60 seconds after the sample contacts the film layer.

When sera are used with different contents of potassium, the following dependence of the reflectance (%R) on the potassium content is found:

TABLE 5

| Potassium content [mmol potassium/l] | Reflectance (% R) |
| --- | --- |
| 0.08 | 63.6 |
| 1.01 | 57.0 |
| 1.98 | 46.3 |
| 3.10 | 37.6 |
| 4.08 | 31.0 |
| 6.08 | 25.0 |
| 8.05 | 22.0 |
| 9.90 | 20.0 |

EXAMPLE 5

4-[2,6-dibromo-4-nitrophenyl)azo]-2-octadecyloxy-1-naphthol a) 2-octadecyloxynaphthalene 172.8 g (1.2 mol) 2-naphthol (98 %) is added to a solution of 48 g (1.2 mol) sodium hydroxide (99 %) in 1 l ethanol in a 4 l three-neck flask with stirrer, cooler and thermometer after it has dissolved 417 g (1.25 mol) n-octadecylbromide are added and the reaction mixture is heated for 14 hours under reflux. After addition of a further 1 l ethanol the hot solution is aspirated over a Seitz filter to remove inorganic material and the weakly pink coloured filtrate is brought to crystallization by placing it is an ice bath for 30 minutes. After aspiration of the almost colourless crystals, the filter cake is washed in portions with ca 700 ml ethanol and after drying over diphosphorus pentoxide, 371.9 g (93.7 % of the theoretical yield) 2-naphthyl-oztadecyl-ether are obtained as colourless crystals, Fp 64–68° C.

TLC: silica gel 60 (Merck), mobile solvent: n-heptane/methyl-ethyl ketone 2:1, $R_f=0.34$ b) 2-octadecyloxy-1-naphthol 594 g (1.5 mol) 2-octadecyloxynaphthalene and 397 g (0.75 mol) lead tetraacetate are added to a mixture of 3 l glacial acetic acid and 600 ml acetic anhydride in a 10 l three-neck flask with stirrer, Claisen attachment, thermometer and cooler with a calcium chloride tube and it is heated to 55° C. Over a period of 4 days a further 400 g lead tetraacetate are added in portions (each of 100 g) at intervals of 24 hours while stirring. Afterwards the yellow solution which is formed is cooled to room temperature, stirred again for 30 minutes after addition of 1.5 l water, the crystal slurry which forms is aspirated and washed in portions with 2 l water. The wet crude product is dissolved in 4 l toluol and shaken three times with 1 l portions of water, three times with 1 l saturated sodium hydrogen carbonate solution and then again three times with 1 l water. After drying the toluol phase over sodium sulphate, aspiration and concentration by evaporation, 635 g brown crude product are obtained which is purified chromatographically as follows: the crystallizate obtained is dissolved in a mixture of 1.3 l toluol/isohexane 5:2 and the solution is applied to a silica gel 60 (Merck) column, inside diameter 11.5 cm, filling height 1.2 m. Toluol/isohexane 5:2 is used as the mobile solvent and fractions of ca 300 ml are taken. Fractions 9–52 are combined and concentrated by evaporation until constancy of weight. One obtains 324.2 g 2-octadecyloxy-1-naphthol acetate, Fp 67–68° C. This is dissolved without further purification in 1.8 l methanol while heating and cooled to 20° C. 93 ml concentrated sulphuric acid are added dropwise within 15 minutes to the suspension which forms without cooling and while stirring, whereby the temperature increases to 35° C. Subsequently it is heated for 2 hours under reflux, then cooled with an ice bath and stirred for a further 30 minutes while cooling on ice. The crystals which form are aspirated, washed with 150 ml ice-cold methanol and dried at 35° C. in a drying cupboard over diphosphorus pentoxide. One obtains 294.4 g (47.5 % of the theoretical yield) 2-octadecyloxy-1-naphthol, colourless crystals, Fp 58–59° C.

c) 4-[(2,6-dibromo-4-nitrophenyl)azo]-2-octadecyloxy-1-naphthol 22.7 g (0.33 mol) sodium nitrite are fed into 300 ml concentrated sulphuric acid in a 2 l three-neck flask with stirrer, Claisen attachment and thermometer during 10–15 minutes while stirring whereby the temperature of the reaction solution is allowed to increase to 35° C. It is then cooled to 20° C. and 230 ml glacial acetic acid are added dropwise in ca 15–20 minutes in such a way that the temperature is held at 20–25° C. while cooling on ice. Afterwards 97.6 ml (0.33 mol) 2,6-dibromo-4-nitroaniline (Riedel de Haen [99 %GC] are added in portions during 10 minutes while cooling occasionally whereby the temperature is kept at 19–21° C. and it is stirred again for a further 3 hours. Afterwards it is poured onto 3.5 l iced water and the diazonium salt solution which forms is added rapidly to a solution of 124 g (0.3 mol) 2-octadecyloxy-1-naphthol in a mixture of 3 l glacial acetic acid and 300 ml chloroform with addition of 180 g (1.33 mol) sodium acetatetrihydrate. (In the production of the solution of the naphthol ether care must be taken that after it has been fed into glacial acetic acid/chloroform with addition of sodium acetate it is again cooled down to 20° C. after a temperature increase to ca. 45° C.) After stirring for 3 hours in the ice bath, the crystallizate which is produced is aspirated, the residue is washed three times with 500 ml water each time and dried in a drying cupboard at 40° C. The crude product —295.5 g light brown crystals —is purified chromatographically. The azo compound is dissolved in 1 l toluol/methylene chloride 2:5 and applied to a silica gel 60 (Merck) column with an inside diameter of 11.5 cm, filling height of 1.2 m and eluted with toluol/methylene chloride 2:5. Fractions of ca. 70 ml are taken. The fractions 57–173 are combined and concentrated by evaporation. One obtains 134.2 g brown crystals. These are dissolved in 480 ml toluol at 80° C., cooled to 65° C. and 800 ml isohexane are added while stirring vigorously. It is allowed to cool to 20° C. while stirring, placed overnight in a refrigerator, the crystals which form are aspirated and the filter cake is washed twice with 300 ml ice-cold toluol/isohexane 1:1.3 and subsequently with 300 ml isohexane. Afterwards it is dried in a drying cupboard at 40° C. over diphosphorus pentoxide until constancy of weight. One obtains 119.9 g (55.5 % of the theoretical yield) light brown crystals of the azo compound, Fp 102–103° C.

The following substance can also be prepared analogous to Example 5a)–c):

d) 4-[(2-bromo-4-nitro-6-trifluoromethylphenyl)azo]-2-octadecyloxy-1-naphthol, Fp 84° C. from 2-bromo-4-nitro-6-trifluoromethylaniline (M. Hauptschein et al., J. Amer. Chem. Soc. 76, 1051 (1954))

EXAMPLE 6

2,4,6,8-tetranitro-5-octadecyloxy-1-naphthol a) 5-octadecyloxy-1-naphthol 40 g (0.25 mol) 1,5-dihydroxynaphthalene (Janssen 99 %) are suspended in 400 ml freshly distilled dimethylformamide in a 2 l three-neck flask with Claisen attachment, thermometer calcium chloride tube and dropping funnel and 6 g (0.25 mol) 97 % sodium hydride is added in small portions within 40 minutes. In this process it becomes dissolved with a blue colour and in addition hydrogen is formed and the temperature increases to 36° C. It is stirred for a further 30 minutes and 83.3 g (0.25 mol) 96 % 1-octadecyl bromide are added dropwise to the 35° C. warm solution within 10 minutes. Subsequently it is stirred again for 24 hours at room temperature. The crude product which is formed is aspirated vigorously and the residue is stirred with 600 ml water for 15 minutes. This procedure is repeated again and the filter residue is washed so long with water (ca. 800 ml) until the filtrate is colourless. Afterwards the filter cake is dried at 40° C. in a drying cupboard over diphosphorus pentoxide. One obtains 98.6 g light beige crystals with a melting point of 76–78° C.

For the further purification, the product is stirred three times with 750 ml of ethyl acetate each time, the undissolved constituents (40.8 g) light beige crystals are filtered off, the mother liquor is treated twice with charcoal and it is concentrated in a vacuum. One obtains 53.2 g (51.9 % of the theoretical yield) beige coloured crystals with a melting point of 90–92° C. This product is used directly for the production of the tetranitrated compound. TLC, silica gel 60 (Merck), mobile solvent: toluol/methanol=50:1, $R_f=0.36$ b) 2,4,6,8-tetranitro-5-octadecyloxy-1-naphthol 1.2 l concentrated sulphuric acid are added to a 2 l three-neck flask with a large stirrer and thermometer, heated to 40° C. and 49.52 g (0.12 mol) 5-octadecyloxy-1-naphthol are added as rapidly as possible while stirring vigorously. After 5–10 minutes a viscous crystal pulp is formed and the temperature increases by 2–3° C. It is then stirred for a further 20 minutes without heating, then cooled to ca. 0° C. and nitrating acid (produced from 34.9 ml nitric acid (65 %) which is added to 70 ml concentrated $H_2SO_4$ within ca. 15 minutes at ca. 10–20° C. while stirring and cooling) is added dropwise at 0–5° C. within 30 minutes. In this process the reaction mixture becomes a grey-brown to red-brown colour. After stirring for a further 4 hours at 5–10° C. it is poured onto ca. 5 kg ice and the crude product is extracted 3 times with 2 l ethyl acetate. Afterwards the ethyl acetate phases are combined, washed twice with 1 l water each time, the ethyl acetate phase is dried over sodium sulphate, aspirated and concentrated by evaporation. Ca. 80 g of a dark-brown resinous residue are obtained. This is purified by column chromatography. A column of 7.5 cm inside diameter, filling height ca. 110 cm, filling material: silica gel 60 (Merck) is used, mobile solvent: toluol/acetone 5:2. Main fraction $R_f=0.24$.

This crude substance is mixed again with ca. 400 ml mobile solvent and if not all is dissolved it is aspirated (the residue can block the column) and the filtrate is applied to the column and eluted in fractions. Fractions of 80 ml each are taken. The forerun (colourless eluate) is ca. 2 l. The fractions containing the substance (30–140) are concentrated by evaporation. 21 g red-brown viscous paste is obtained which crystallizes out after standing for a long period. This product is dissolved in 42 ml acetone and the final product is precipitated by slow addition of the 5-fold amount of isohexane at room temperature. After stirring for five hours it is aspirated, the filter cake is washed with isohexane and dried in a vacuum over diphosphorus pentoxide and a molecular sieve at room temperature. 14.9 g (21 % of the theoretical yield) of the desired tetranitro-octadecyloxy-naphthol is obtained, Fp 236–233° C. (decomp.). TLC: silica gel 60 (Merck), mobile solvent: methylene chloride/methanol 8:1; $R_f=0.27$.

EXAMPLE 7

3-pentadecyl-2,4,6-trinitrophenol 67.5 g (0.2 mol) pentadecylphenol (90 %) is added while stirring to 100 ml concentrated sulphuric acid in a 500 ml Erlenmeyer flask, heated to 90° C., whereby a dark-brown, highly viscous paste is formed which is difficult to stir and this is kept at 90° C. for 1 hour. In a separate 1 l three-neck flask 70 ml (ca. 1 mol) 65 % nitric acid is cooled to 1020 C. with the aid of an ice bath. The highly viscous sulfonation product obtained previously is added in small portions to the nitric acid during ca. 2 hours (whereby the viscous paste is kept liquid with a hair drier) while cooling with an ice bath in such a way that the temperature does not exceed 25° C. and in this process a beige-coloured paste which is difficult to stir is obtained which is stirred for a further hour at room temperature. Afterwards it is poured onto 500 g ice and while doing so a fine precipitate forms. The crude product obtained in this way can only be aspirated with difficulty which is why the total preparation is preferably centrifuged. After decanting off the supernatant liquid, this procedure is repeated twice after addition of water each time in order to remove adhering acid; the resulting precipitate is rinsed into a flask with 500 ml ethanol, dissolved by heating to 50° C. (in a water bath) and crystallized by placing it in an ice bath. After vigorous aspiration of the product one obtains 37.5 g (42.6 % of the theoretical yield) of a weakly beige-coloured 3-pentadecyl-2,4,6-trinitrophenol which is moist with ethanol, melting point 53–56° C., TLC: silica gel 60, mobile solvent: ethyl acetate/methanol/glacial acetic acid 90:5:5, $R_f=0.8$.

After drying the substance over diphosphorus pentoxide one obtains 35.75 g (40.1 % of the theorectical yield) 3-pentadecyl-2,4,6-trinitrophenol, Fp 59–61° C.

EXAMPLE 8

[(2,4-dinitrophenyl)hydrazonolprooanedinitrile 2.1 g (0.03 mol) sodium nitrite are dissolved in 30 ml concentrated sulphuric acid. During this the temperature increases to 50° C. It is cooled to 20° C., 20 ml glacial acetic acid are added dropwise at 15–20° C. and 5.5 g (0.03 mol) 2,4-dinitroaniline (NL-A-6411189) are added in portions and it is stirred again for a further one hour at 20° C.

1.98 g malodinitrile is dissolved in 75 ml ethanol, a solution of 74 g sodium acetate-trihydrate in 35 ml water is added and the diazonium salt solution produced above is added dropwise while stirring at 19° C.

After 1 hour the reaction mixture is purified chromatographically on silica gel 60 (Merck) with methylene chloride/methanol=98:2, yielding the product with $R_f=0.28$.

We claim:

1. A test carrier useful in determining a specific ion in a liquid sample comprising:
   a porous film layer having a liquid resistant organic phase which contains a homogeneous mixture of
   (i) a hydrophobic polymer,
   (ii) a plasticizer,
   (iii) an ionophore,
   (iv) a substance which changes color in the presence of the ion to be determined, and
   (v) a plurality of particles having an oil absorption value from 80–200, wherein said ionophore is homogeneously dispersed in said organic phase.

2. Test carrier of claim 1, wherein said hydrophobic polymer is a copolymer of vinyl acetate.

3. The test carrier of claim 1 comprising porous particles.

4. Test carrier of claim 1, wherein said hydrophobic polymer and said plurality of particles are present in a weight ratio ranging from about 5:1 to about 1:10.

5. Test carrier of claim 4, wherein said weight ratio ranges from about 1:1 to about 1:3.

6. Test carrier of claim 1, wherein said plasticizer is selected from the group consisting of a setacic acid ester, a phthalic acid ester, an acrylic acid ester, a phosphoric acid ester and a silicon.

7. Test carrier of claim 1, wherein said hydrophobic polymer and said plasticizer are present in a weight ratio ranging from about 5:1 to about 1:5.

8. Test carrier of claim 7, wherein said weight ratio is from about 2:1 to about 1:2.

9. Test carrier of claim 1, wherein said substance which changes color is of the formula wherein $R^1$, $R^2$ and $R^3$ are the same or different and are selected from the group consisting of hydrogen, an alkyl group and a alkoxy group, wherein at least one of $R^1$, $R^2$ and $R^3$ is an alkyl or alkoxy group having from 8 to 30 carbons, $R^4$ is hydrogen or an alkyl group, $R^5$ is a nitro group, an alkyl group substituted by halogen, a cyano group, a sulfonamide group or an alkyl sulfonyl group, X is nitrogen or $CR^6$, and Y is sulphur or $CR^7=CR^8$ wherein $R^6$, $R^7$ and $R^8$ are the same or different and are selected from the group consisting of hydrogen, halogen, a nitro group, a cyano group, an unsubstituted alkyl group, an alkyl group substituted by halogen and an alkyl sulfonyl group.

10. The test carrier of claim 1 wherein said test layer further comprises an alkyl phenol having at least two nitro groups, an alkoxynaphthol having at least two nitro groups or a carbonyldicyanidophenyl hydrazone.

11. The test carrier of claim 1 wherein said test layer further comprises a buffer capable of maintaining the pH at a value of between 5–10.

12. A test carrier useful in determining a specific ion in a liquid sample comprising:
(a) a first test layer which is a porous film layer having a liquid resistant organic phase which contains homogenous mixture of:
(i) a hydrophobic polymer,
(ii) a plasticizer,
(iii) an ionophore, and
(iv) a plurality of particles having an oil absorption value of from 80–200, wherein said ionophore is homogeneously dispersed in said organic phase, and
(b) a second test layer containing a substance which changes color in the presence of said specific ion, wherein said first and second layers are positioned in said test carrier to permit fluid contact therebetween.

13. Method for determining a specific ion in a liquid sample comprising contacting said liquid sample to the test carrier of claim 1 and determining a change in color of said substance which changes color in the presence of said specific ion.

14. Method for determining a specific ion in a liquid sample comprising contacting said liquid sample to the test carrier of claim 12 and determining a change in color of said substance which changes color in the presence of said specific ion.

15. Method of claim 13, comprising determining said change in color about 60 seconds after contacting the liquid sample thereto.

16. Method of claim 14, comprising determining said change in color about 60 seconds after contacting the liquid sample thereto.

17. Test carrier of claim 1 wherein the plasticizer is 2,2-diphenyl-1-cyano-acrylic acid-ethylhexylester.

* * * * *

UNITED STATES PATENT AND TRADEMARK OFFICE
CERTIFICATE OF CORRECTION

PATENT NO. : 5,211,914
DATED : May 18, 1993
INVENTOR(S) : Peter Vogel, et al.

It is certified that error appears in the above-indentified patent and that said Letters Patent is hereby corrected as shown below:

Col. 4, line 1: delete "practicle" and insert -- practical --.

Col. 4, line 2: delete "rut" and insert -- out --.

Col. 9, line 37: delete "said" and insert -- salt --.

Signed and Sealed this

Sixth Day of September, 1994

Attest:

BRUCE LEHMAN

*Attesting Officer*       *Commissioner of Patents and Trademarks*